United States Patent [19]
Yokomizo et al.

[11] Patent Number: 5,772,682
[45] Date of Patent: Jun. 30, 1998

[54] NOSE RAISING ORTHOPEDIC DEVICE

[75] Inventors: Masanobu Yokomizo, 4-13, Chikko, Wakayama-shi, Japan, 640; Toshiharu Yokomizo, Koto-ku, Japan

[73] Assignee: Masanobu Yokomizo, Wakayama, Japan

[21] Appl. No.: 729,025

[22] Filed: Oct. 10, 1996

[30]     Foreign Application Priority Data

Jun. 19, 1996  [JP]  Japan ..................................... 8-158341

[51] Int. Cl.$^6$ .................................................. A61B 17/00
[52] U.S. Cl. ...................................................... 606/204.45
[58] Field of Search ....................... 254/18, 22; 606/104, 606/101, 205–211, 204.45

[56]             References Cited

U.S. PATENT DOCUMENTS 321,721   7/1885  Hasan ....................................... 606/174
4,798,366  1/1989  Pearson et al. ........................... 254/22

FOREIGN PATENT DOCUMENTS 60-153807  8/1960  Japan .
57-49929  11/1982  Japan .

*Primary Examiner*—Michael Powell Buiz
*Assistant Examiner*—William W. Lewis
*Attorney, Agent, or Firm*—Wenderoth, Lind & Ponack, L.L.P.

[57]            ABSTRACT

A nose orthopedic device includes a pair of raiser arms having pressing tab portions provided at respective distal ends thereof. A resilient device is provided between the two raiser arms for urging the pressing tab portions against each other. The pressing tab portions are moved into contact with and separated from each other by the operation of the two raiser arms.

8 Claims, 2 Drawing Sheets

NOSE RAISING ORTHOPEDIC DEVICE

BACKGROUND OF THE INVENTION

The present invention relates to a nose raising orthopedic device capable of raising the nose and reducing the nares of a person who wishes to a higher, well-shaped nose.

Generally speaking, women who have a desire to be more beautiful and some who are strongly determined person undergo cosmetic orthopedic surgery for nose raising or nose reshaping. A cosmetic orthopedic surgery operation includes transplanting a part of the cartilage of an ear to a small, upward nose, grinding a part of the nasal bone of an aquiline nose for lowering, or implanting a dose of ceramic, apatite, kilbone, or atex material in the nose for shaping. If the nose is snub or blunt with its alae extending outward, its vestibulal mucous at the ala sides is partially removed and stretched to narrow the nares. However, such a cosmetic orthopedic surgery operation is costly and painful, and thus can hardly be recommended to every patient.

For compensation, a variety of simple nose raising devices or tools have been developed including such as disclosed in Japanese Patent Laid-open Publication No. 60-153807 (referred to hereinafter as first prior art arrangement) and Japanese Utility-model Publication No. 57-49929 (referred to hereinafter as second prior art arrangement). The nose raiser of the first prior art arrangement comprises two half-round members mounted to the distal end of an arm and equipped with a spring. The nose raiser is inserted into the nares of raising with a yielding force of the spring. The nasal orthopedic device of the second prior art arrangement is adapted for raising the back of a nose with a bar member turning about a fulcrum on the face bone.

To be positioned in a nose, the nose raiser of the first prior art arrangement has to be gripped on the periphery of fingers and expansively inserted in its standing state into the nares which are wet and slippery. Hence it is likely that such nose raiser will be inserted into the nose and correct positioning of the nose raiser in the nose will be troublesome. As the nares are wet and slippery, the nose raiser may be caused to fall by a small movement of a facial muscle. During inserting or removing of the nose raiser, the fingers of an operator move into the nose, and such will be adverse to sanitary safety.

The nasal orthopedic device of the second prior art arrangement has a pressing strip and a supporting strip provided for coming into direct contact with two, i.e. upper and lower, respective regions of the vestibulal wall, thus preventing the device from falling down in the nose. However, similar to the first prior art arrangement, the nasal orthopedic device of the second prior art arrangement has to be gripped on the periphery by fingers and inserted with equal difficulty into the nares which are wet and slippery. During inserting or removing of the nasal orthopedic device, the fingers of an operator move into the nose and will be adverse to sanitary safety. It is also difficult for the pressing strip of the device to be set against the upper region of the vestibulal wall of the nares to apply a generously controlled pressure.

The present invention is developed in view of the above, and the object of the invention is to provide a nose raising orthopedic device which can, with ease, be inserted into and removed from the nose of any person who wishes to have his or her nose reshaped beautifully by raising and shaping the nose while narrowing its nares, thus eliminating the disadvantages of the prior art.

SUMMARY OF THE INVENTION

For achievement of the above object of the present invention, a nose raising orthopedic device comprises a pair of raiser arms, each having at its distal end a pressing tab portion. A resilient device is provided between the two raiser arms for urging the pressing tab portions against each other. The pressing tab portions can be in contact with and be separated from each other by actions of the two raiser arms.

Also, the nose raising orthopedic device includes a through aperture provided in the pressing tab portion of each raiser arm for flow of air. Further, weights are loadable onto lower end of the respective two raiser arms.

DETAILED DESCRIPTION OF THE PREFERRED EMBODIMENT

One preferred embodiment of the present invention will be described in more detail.

Figure 1:
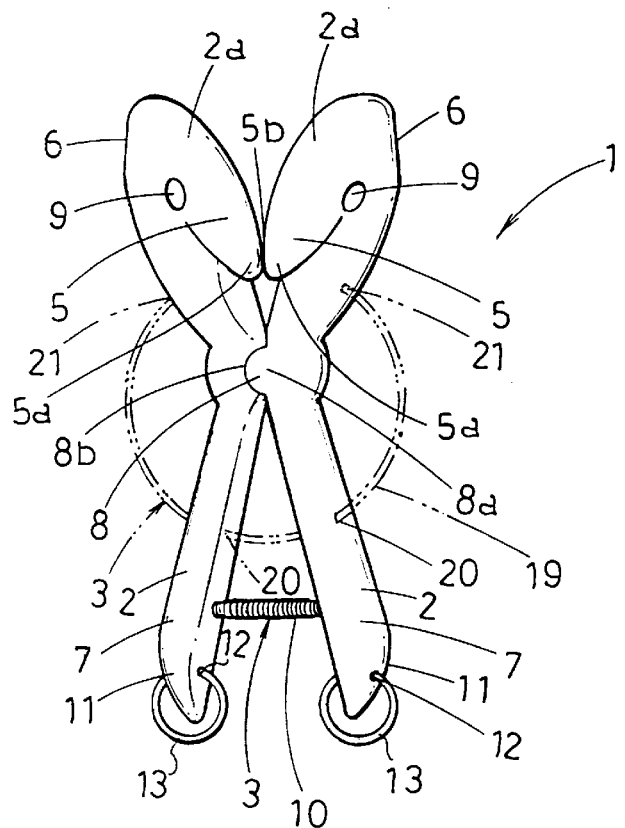
FIG. 1 is a perspective view of a nose raising orthopedic device according to the present invention.
Figure 2:
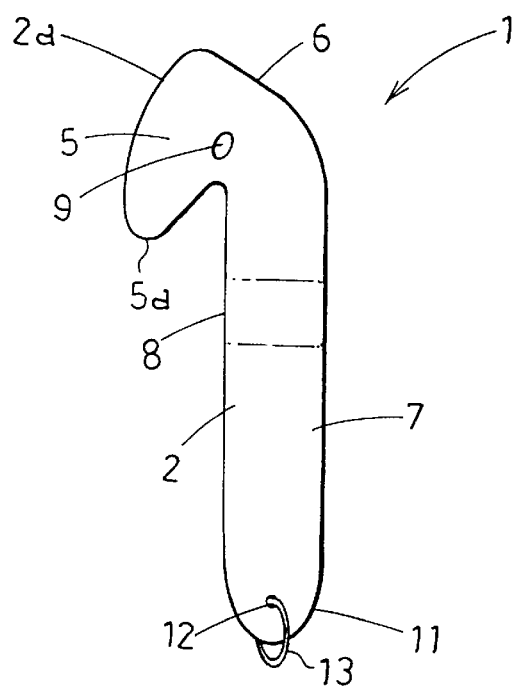
FIG. 2 is a perspective view of a raiser arm, seen from one side, of the device of the present invention.
Figure 3:
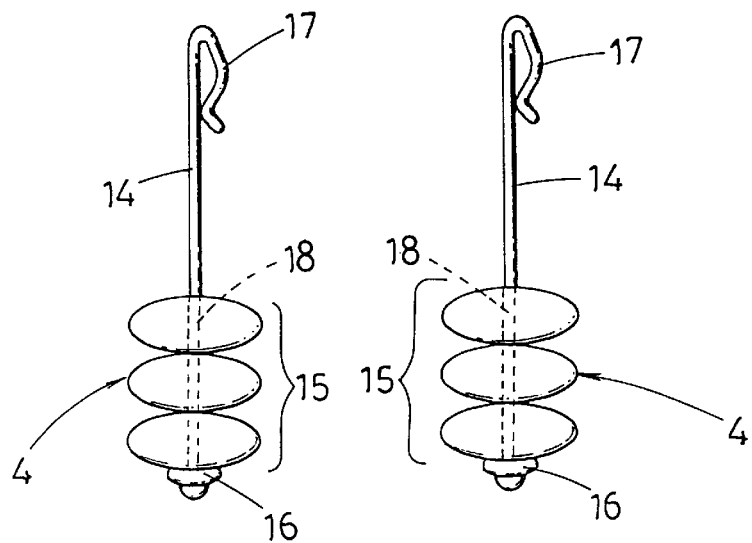
FIG. 3 is a perspective view of a pair of weights of the device of the present invention.
Figure 4:
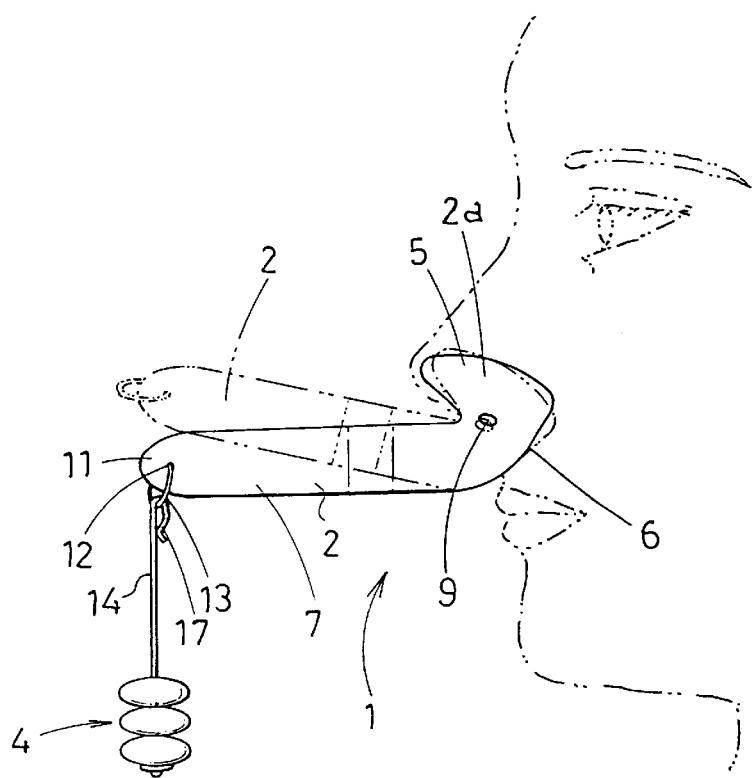
FIG. 4 is an explanatory view showing the nose raising orthopedic device of the present invention in use.

As shown in FIGS. 1 to 4, a nose raising orthopedic device 1 of the present invention comprises a pair of raiser arms 2, a resilient device 3, and a pair of weights 4.

Each raiser arm 2 has a pressing tab 5 of a modified conical shape provided on a distal end 2a thereof for ease of inserting into the naris of a human nose. More specifically, the pressing tab 5 is radially enlarged from its tip end 5a and has a flattened upper rear edge 6. The raiser arm 2 is V-shaped having one side or leg including the pressing tab 5 and the upper rear edge 6. A grip 7 is provided at the other side or leg of the V shape and has a flat inner side and a rounded outer side for ease of gripping.

The two V-shaped raiser arms 2 are joined to each other at a joint 8. One of the raiser arms has an engaging recess 8b while the other has an engaging projection 8a. As the engaging projection 8a is fitted into the engaging recess 8b, the two raiser arms 2 are joined together so that their respective pressing tabs 5 are movable toward and away from each other. The pressing tabs 5 of the two raiser arms 2 come into direct contact with each other at inner sides 5b of their tip ends 5a. Each pressing tab 5 also has therein a through aperture 9 for passage of air flow. More than one aperture 9 may be provided and the size and shape thereof are not limited.

A coil spring 10 acts as the resilient device 3 and is mounted between the inner sides of the two raiser arms 2. The grips 7 are urged outwardly in opposite directions by the force of the coil spring 10, and simultaneously the pressing tabs 5 of the raiser arms 2 are forcedly kept in contact with each other.

Each raiser arm 2 has a hole 12 provided in a bottom portion 11 thereof for accepting and engaging with a ring 13. The ring 13 is used for suspending a respective weight 4 when required. The weight 4 comprises a shaft 14, one or more weight pieces 15, a stopper 16, and a hook 17 formed by folding an upper end of the shaft 14. Each weight piece 15 has a center bore 18 provided therein through which the shaft 14 extends to the stopper 16. Accordingly, the weight pieces 15 are securely sustained by the shaft 14 and are prevented by the stopper 16 from dropping off shaft 14. The stopper 16 is threaded onto the lowermost end of the shaft 14, thus allowing loading and unloading a desired number of the weight pieces 15 for weight control.

The resilient device 3 is not limited to the coil spring 10 but may be a resilient wire 19 of a partially cutoff ring shape arranged to urge the two pressing tabs 5 of the raiser arms 2 to remain in contact with each other. More particularly, the resilient wire 19 extends through holes 20 provided in the grips 7 of their respective raiser arms 2 and presses directly with both cutoff ends 21 against corresponding regions of the raiser arms 2 adjacent to the upper rear edges 6.

In operation, the nose raising orthopedic device 1 of the embodiment is gripped at the grips 7 of the two raiser arms 2 while resisting the yielding force of the coil spring 10 so as to separate the pressing tabs 5 from each other. The pressing tabs 5 while being separated are slowly inserted into the nares of a user with upper rear edges 6 sliding directly on the inner walls of the entrances of the nares. When the pressing tabs 5 are in the nares, their tip ends 5a come into direct contact with upper regions of the vestibulal walls.

Upon the grips 7 being released, the force of the coil spring 10 presses the pressing tabs 5 against the center partition of the nose. Then, the rear ends of the two pressing arms 2 are lowered towards the mouth or the weights 4 are loaded with their hooks 17 engaged with the rings 13 of the pressing arms 2. As the pressing arms 2 move downward, their pressing tabs 5 are lifted upward by being turned about the respective upper rear edges 6, thus causing the tip ends 5a to press against the upper regions of the vestibulal walls in the nose. This pressing up action contributes to raising the nose to a desired shape and narrowing the nares to a small, generous size.

The control over stress and angle of the pressing tabs 2 to the upper regions of the vestibulal walls in the nose will be executed with ease. The nose raising orthopedic device 1 may be provided of different sizes, for example, large, medium, and small, in which the pressing tabs 5 are modified in length, width, and angular configuration to match the shapes of individual noses. The pressing tabs 5 are inserted into or removed from the nares with no fingers touching the inside of the nose, hence improving sanitary conditions.

What is claimed is:

1. A nose raising orthopedic device comprising:
    a pair of raiser arms, each said raiser arm having at a first end thereof a pressing tab portion fittable into a naris of a human, and each said raiser arm having at a second end thereof a grip;
    a resilient device acting on said raiser arms to move said raiser arms relative to each other in a first direction to continuously urge said pressing tab portions toward each other; and
    said pressing tab portions being separable from each other by movement of said grips to move said raiser arms against the force of said resilient device in a second direction opposite to said first direction.

2. A nose raising orthopedic device as claimed in claim 1, wherein each said pressing tab portion has therethrough an aperture for flow of air.

3. A nose raising orthopedic device as claimed in claim 2, further comprising means for loading weights onto respective said second ends of said raiser arms.

4. A nose raising orthopedic device as claimed in claim 1, further comprising means for loading weights onto respective said second ends of said raiser arms.

5. A nose raising orthopedic device as claimed in claim 1, wherein each said pressing tab portion is radially enlarged from a tip end thereof and has a flattened rear edge.

6. A nose raising orthopedic device as claimed in claim 1, wherein said resilient device comprises urging said grips away from each other.

7. A nose raising orthopedic device as claimed in claim 1, wherein said resilient device comprises a resilient wire member of partially cut-away ring shape, said wire member extending through holes in said grips and having opposed free ends pressed against respective said raiser arms adjacent said first ends thereof.

8. A nose raising orthopedic device as claimed in claim 1, wherein said raiser arms are pivotally connected at a joint between respective said first and second ends thereof.

* * * * *